(12) United States Patent
Burbar et al.

(10) Patent No.: US 11,375,966 B2
(45) Date of Patent: Jul. 5, 2022

(54) PATIENT DISPLAY SYSTEM FOR A MEDICAL IMAGING OR RADIOTHERAPY APPARATUS

(71) Applicants: Siemens Medical Solutions USA, Inc., Malvern, PA (US); The Trustees of the University of Pennsylvania, Philadelphia, PA (US)

(72) Inventors: Ziad Burbar, Knoxville, TN (US); Inki Hong, Knoxville, TN (US); Stefan B. Siegel, Knoxville, TN (US); Joel Karp, Glenside, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/949,296

(22) Filed: Oct. 23, 2020

(65) Prior Publication Data

US 2022/0125395 A1 Apr. 28, 2022

(51) Int. Cl.
*A61B 6/00* (2006.01)
*A61B 6/04* (2006.01)

(52) U.S. Cl.
CPC .......... *A61B 6/461* (2013.01); *A61B 6/0407* (2013.01); *A61B 6/4447* (2013.01); *A61B 6/4458* (2013.01); *A61B 6/5235* (2013.01)

(58) Field of Classification Search
CPC ............ A61N 5/1048; A61N 5/1049; A61N 2005/1056; A61B 6/04; A61B 6/0407; A61B 6/0492; A61B 6/08; A61B 6/44; A61B 6/4429; A61B 6/4435; A61B 6/46; A61B 6/461; A61B 6/462; A61B 6/464; A61B 6/5235; A61B 6/5294
See application file for complete search history.

(56) References Cited

U.S. PATENT DOCUMENTS

| 5,134,373 | A | * | 7/1992 | Tsuruno | G01R 33/283 |
|---|---|---|---|---|---|
| | | | | | 324/309 |
| 5,151,722 | A | | 9/1992 | Massof et al. | |
| 5,877,732 | A | | 3/1999 | Ziarati | |
| 6,774,929 | B1 | * | 8/2004 | Kopp | A61B 5/055 |
| | | | | | 345/8 |
| 9,541,613 | B2 | * | 1/2017 | Lee | G01R 33/34046 |
| 10,241,160 | B2 | * | 3/2019 | Lee | A61B 5/055 |
| 2018/0000435 | A1 | * | 1/2018 | Liu | A61B 6/032 |

FOREIGN PATENT DOCUMENTS

WO WO-2014193796 A1 * 12/2014 ............. A61B 6/461

* cited by examiner

*Primary Examiner* — Anastasia Midkiff (57) ABSTRACT

A medical imaging and/or radiotherapy apparatus incorporates a display for projecting a visible image to a patient lying on a patient table. A projector that projects the visible image moves in tandem with the patient table, so that it appears relatively motionless to the patient. In exemplary embodiments, the projector projects the visible image within a patient tunnel of the medical apparatus, including in some embodiments, an extended field of view medical imaging apparatus. In other exemplary embodiments, the projector projects the visible image on a screen above the patient table of a tunnel-less medical apparatus. The projector remains outside the imaging line of response of detectors within the imaging field or outside of the radiotherapy beam zone, to avoid potential degradation of the captured diagnostic image or degradation of the radiotherapy beam.

23 Claims, 4 Drawing Sheets

PATIENT DISPLAY SYSTEM FOR A MEDICAL IMAGING OR RADIOTHERAPY APPARATUS

STATEMENT REGARDING FEDERALLY SPONSORED RESEARCH

This invention was made with government support under CA225874 awarded by the National Institutes of Health. The government has certain rights in the invention.

TECHNICAL FIELD

This disclosure relates to medical imaging and/or radiotherapy apparatus incorporating a display for projecting information visible to a patient during an imaging procedure. More particularly, in some embodiments, the patient display projects video images that are visible to a patient while within a patient tunnel of such medical apparatus.

BACKGROUND

Diagnostic medical imaging apparatuses include, by way of non-limiting example, computed tomography (CT), two-dimensional digital radiography (DR), magnetic resonance imaging (MRI), positron emission tomography (PET), and single photon emission computed tomography (SPECT) modalities. Hybrid modality apparatuses include, by way of non-limiting example, PET/CT, PET/MRI, SPECT/CT and SPECT/MRI, which combine in a single system the local imaging resolution benefits of CT or MRI and the sensitivity for imaging and detecting cellular and metabolic biological processes in a patient. Some embodiments of medical radiotherapy apparatus incorporate linear accelerators or other devices to emit electromagnetic or other forms of radiation, or particles (e.g., electrons, protons, or neutrons) for oncology therapy. Some hybrid imaging/radiotherapy medical apparatus provide image-guided radiation therapy by combining a medical imaging apparatus (e.g., MRI, PET, CT modalities) with a linear accelerator or other therapeutic radiation beam generating apparatus. Many of the aforementioned medical imaging apparatuses or systems (with or without radiotherapy treatment capabilities) include a toroidal-shaped gantry structure with a central imaging tunnel, through which is inserted a translatable patient table. The gantry also includes one or more electromagnetic radiation detectors, which emit electrons in response to incident photons of electromagnetic radiation. In some modalities, the incident photons are transmitted X-rays or ionized radiation emissions at the higher end of the electromagnetic frequency range (e.g., CT, DR, PET, SPECT), while in other modalities (e.g., MRI) the incident photons are within the radio frequency range. The output electrons of the detector are processed by detector electronics to generate detector output signals, which are subsequently processed by the imaging apparatus to generate or construct patient images. In some imaging systems, detector electronics packages are housed with the detectors within the gantry structure in an integrated detector assembly. Some radiotherapy apparatus also incorporate patient tunnels.

Some patients undergoing diagnostic imaging or radiotherapy procedures experience claustrophobia or other forms of anxiety or other emotional discomforts, which may arise from the prospect of having to go through the procedure itself, or upon application of immobilization devices during the procedure to avoid patient movement, or when they are positioned in the relatively narrow confines of an imaging tunnel or a patient tunnel. Patient tunnel lengths are increasing from approximately one to two meters as newer generations of imaging apparatus are expanding their axial field of view (FOV). For example, combined PET/CT imaging systems share a common imaging tunnel, with sequentially aligned PET and CT imaging fields. Anxiety or other emotional discomforts of patients who were uncomfortable in one-meter imaging or patient tunnels can increase when they are placed in longer one- to two-meter FOV imaging tubes, such as those in PET/CT systems—whether from a heightened sense of claustrophobia or perceived greater sense of darkness. Other patients who tolerated placement in shorter one-meter imaging tubes experience anxiety or other emotional discomforts in the longer FOV imaging tubes. Yet other patients are uncomfortable with repeated back-and-forth motion of the patient table during scanning procedures. Some medical imaging procedures are lengthy, increasing likelihood that the patient will experience of one or more of impatience, involuntary movement, attention deficit, or dissatisfaction. All the above negative emotional experiences are especially acute for pediatric patients.

During some medical imaging and/or radiotherapy procedures, patients are given oral information, such as time remaining before the end of the procedure, or sequential instructions to remain still or hold their breath. It is difficult to hear oral instructions from within a patient tunnel, especially in view of background noise generated in the tunnel by system components during a scanning or radiotherapy procedure, especially for patients with impaired hearing.

SUMMARY

Exemplary embodiments of a medical imaging and/or radiotherapy apparatus described herein incorporate a display for projecting a visible image that is visible to a patient lying on a patient table, during a diagnostic imaging or radiotherapy procedure. In some embodiments, the projected visual image moves in tandem with the patient table, so that it appears relatively motionless to the patient. In exemplary embodiments, the visible image is projected within a scanning or patient tunnel of an extended field-of-view, medical-imaging apparatus or radiotherapy. In tunnel-less medical imaging or radiotherapy apparatus exemplary embodiments, the visible image is projected on a screen or other surface (e.g., a wall or ceiling in the imaging room) above the patient table, moving in tandem with the patient table. In some embodiments, the projected image includes one or more of patient instructions, mood-enhancing images or lighting, or entertainment videos.

By moving the projected displayed image in tandem with a moving patient table of the medical apparatus, it appears to the patient's eyes to be in a relatively fixed position. This reduces likelihood of patient eye strain, motion sickness, or involuntary movement that might otherwise occur if the projected image appears to bounce around on the inner surface of the patient tube or on an overhead screen. Stationary appearing, written image instructions are easily readable by a patient, obviating the need to shout or broadcast with a loudspeaker, oral procedural instructions to the patient within a patient tube. Stationary projected image clarity allows patients to enjoy relaxing entertainment videos and/or mood lighting to help avoid or overcome one or more of anxiety, impatience, involuntary movement, and general dissatisfaction during the procedure.

In embodiments disclosed herein, the projector used to project visual images is located outside a medical scanner's imaging line of response of detectors that are acquiring patient image data during a scanning procedure. In this orientation, the projector does not potentially degrade the patient image data and the reconstructed image, because its physical structure does not interfere with electromagnetic scanning transmissions in the active scanning field of view, or hamper ability of active radiation detectors in the FOV to detect those transmissions. In embodiments disclosed herein the projector is located outside a radiotherapy apparatus' transmitted radiation beam zone, so as not to disrupt the beam(s).

In some embodiments, the projector is coupled directly to a stationary (i.e., static) or translatable patient table (e.g., at the head or foot end of the table) and projects the visual image into the patient/imaging tunnel or on a screen above the patient table. In some embodiments, the screen is a portion of the ceiling of the imaging room that houses the imaging and/or radiotherapy apparatus. In this way, the projected visual image of the projector moves in tandem, at the same velocity as the moving table. In other embodiments, the projector is coupled to a translatable track or robot arm that moves the projected visual image of the projector in tandem with, at the same velocity, as the patient table.

Exemplary embodiments disclosed herein feature a patient display system for a medical imaging apparatus. The apparatus includes a gantry, generating an imaging line of response in a diagnostic imaging field. A patient table is selectively translatable through the diagnostic imaging field of the gantry, at a first velocity, though in some embodiments, the patient table is stationary in a scanning procedure. A translatable visual image projector, accessing a visual image, projects the visual image above the patient table in a location that is visible to a patient lying on a patient table. The projector translates in tandem with the patient table, so that the projected visual image translates in tandem at the first velocity and appears motionless relative to the patient table. In imaging apparatus having static patient tables, the projector is also static. However, whether the patient table is static or translatable, the projector always remains outside the imaging line of response in the imaging field where the imaging apparatus is acquiring patient image data.

Other exemplary embodiments disclosed herein feature a method for displaying a visual image to a patient during a diagnostic imaging scanning procedure with a medical imaging apparatus. The method is practiced with the medical imaging apparatus by generating an imaging line of response in a diagnostic imaging field with a gantry of the medical imaging apparatus. A patient, on a patient table, is selectively translated at a first velocity, through the diagnostic imaging field generated by the gantry, so that the apparatus acquires patient image data in the imaging line of response. In some embodiments, the patient table is stationary during an imaging procedure, so its velocity is zero. A translatable visual image projector projects an acquired visual image above the patient table in a location that is visible to a patient lying on a patient table. The visual image projector is located outside the imaging line of response when the apparatus is acquiring image data. The projector is translated in tandem with the patient table, so that the projected visual image translates in tandem at the first velocity and appears motionless relative to the patient. table. The projector always remaining outside the imaging line of response in the imaging field when it is acquiring patient image data.

Additional exemplary embodiments disclosed herein feature a patient display system for a dual modality, PET/CT medical imaging apparatus. The medical imaging apparatus comprises a gantry including an extended field-of-view imaging tunnel, which in some embodiments, has an axial length greater than one meter. The gantry is capable of generating, through the imaging tunnel, a first imaging line of response in a PET diagnostic imaging field; and a second imaging line of response in a CT diagnostic imaging field that is axially adjacent to the PET imaging field. A patient table is selectively translatable, at a first velocity, through the imaging tunnel, in either of the diagnostic imaging fields. A visual image projector, accessing a visual image, projects an acquired visual image on a wall of the imaging tunnel, in a location that is visible to a patient lying on the patient table. The projector translates in tandem with the patient table, so that the projected visual image translates in tandem at the first velocity and appears motionless relative to the patient table. The projector always remains outside the respective imaging line of response of one of the respective imaging fields, when it is acquiring patient image data.

The respective features of the exemplary embodiments that are described herein may be applied jointly or severally in any combination or sub-combination.

BRIEF DESCRIPTION OF DRAWINGS

The exemplary embodiments are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Exemplary embodiments of the patient displays for medical imaging and/or radiotherapy systems described herein project a visible image to a patient lying on a translatable patient table of the system. In embodiments incorporating a translating or otherwise moving patient table, as opposed to a stationary or static patient table, the projected visible image moves in tandem with the patient table, so that it appears relatively motionless to the patient. In exemplary embodiments, the visible image is projected within a patient tunnel, which is sometimes referred to as an imaging tunnel or a scanning tunnel; whether in a standard or in an extended field of view medical imaging and/or radiotherapy apparatus. In other exemplary embodiments, the visible image is projected on a screen above the patient table of a tunnel-less medical imaging and/or radiotherapy apparatus. Medical imaging apparatuses include, by way of non-limiting example, computed tomography (CT), two-dimensional digital radiography (DR), magnetic resonance imaging (MRI), positron emission tomography (PET), and single photon emission computed tomography (SPECT) modalities. These patient displays are also utilized in hybrid modality apparatuses, including by way of non-limiting example, PET/CT, PET/MRI, SPECT/CT, and SPECT/MRI imaging systems. Many of the imaging apparatuses or systems include a toroidal-shaped gantry structure with a central imaging tunnel, through which is inserted the translatable patient table. The gantry also includes one or more electromagnetic radiation detectors, which emit electrons in response to incident photons of electromagnetic radiation. Some embodiments of radiotherapy apparatuses incorporate a gantry and patient tube, around which moves a linear accelerator or other radiation beam generating apparatus and a translatable or stationary patient table, while others have open gantries supporting the beam generating apparatus.

The patient display system comprises a projector that is located outside the medical scanner's imaging line of response of detectors that are in use during an imaging scanning procedure. In all the described imaging apparatuses, it is desirable to avoid placement of anything other than the patient in the medical scanner's imaging line of response of detectors, to minimize distortions in scanning images. When other objects are located in the active scanning field of view (FOV) of the medical imaging apparatus, they have the potential to interfere with electromagnetic scanning transmissions and/or hamper ability of active radiation detectors in the FOV to detect those transmissions. Similarly, in radiation therapy apparatus, the projector is located outside the radiation beam transmission field, to avoid disruption of the transmitted beam.

The projector of the patient display system moves in tandem with the patient table of the imaging and/or radiotherapy system, at the same speed and direction, so that the projected image appears to the patient to be in the same constant position relative to her or his eyes. The constant relative orientation position of the projected image helps mitigate tendency of a patient to move or feel motion sickness compared to viewing a projected that bounces around above the patient table. In some embodiments, tandem movement of the patient table and the projector is accomplished by mounting or otherwise coupling the projector directly to the patient table. In other embodiments, the projector is coupled to a translatable track or arm that moves the projector in tandem with and at the same velocity as the patient table. In imaging and/or radiotherapy apparatus that incorporate a stationary or static patient table, the projector is also stationary, and located outside the medical scanner's imaging line of response of detectors that are in use during an imaging scanning procedure and outside the radiotherapy radiation beam transmission field.

In FIGS. 1-5, an extended FOV, PET/CT, dual-modality imaging apparatus or system 10 includes a gantry 12, which incorporates a cylindrical-shaped, imaging tunnel 14, sometimes referred to as an imaging passage. Axial end covers of the gantry are removed, exposing an imaging tunnel wall 16. The gantry 12 defines PET scanning field 18 and a CT scanning field 20. A patient table 22 is located in the imaging tunnel 14, and is translatable along a translation axis X, to move a patient P axially through the PET scanning field 18 and/or the CT scanning field 20. Patient image data are acquired by radiation detectors located in an imaging line of response within the PET scanning field 18 or within the CT scanning field 20. More specifically, the PET scanning field 18 is established within the axial length of a radiation detector array 26, comprising a plurality of axially aligned rows and circumferentially aligned columns of radiation detector heads. The imaging apparatus 10 is constructed and operated in known fashion to obtain PET and/or CT images of the patient P. The patient table 22 is of known construction and operation, so specific details concerning its translation motion control are not described.

Figure 2:
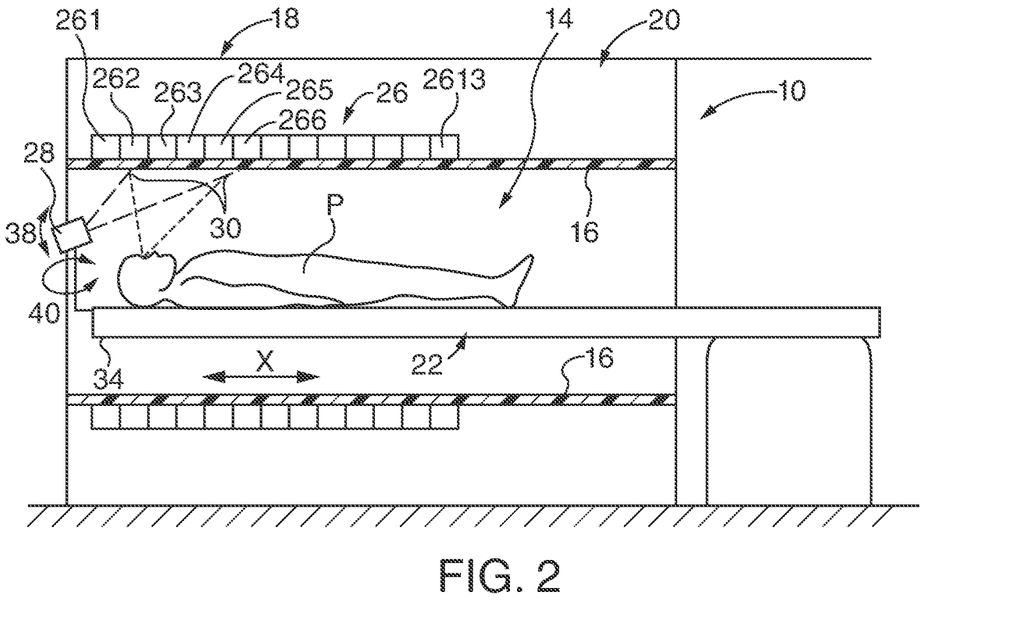
FIG. 2 is an axial cross-sectional view of the medical imaging apparatus of FIG. 1, showing a patient on a patient table in a first axial scanning position in the PET scanning portion of its imaging tube taken along cut line 2-2 of FIG. 1.
Figure 3:
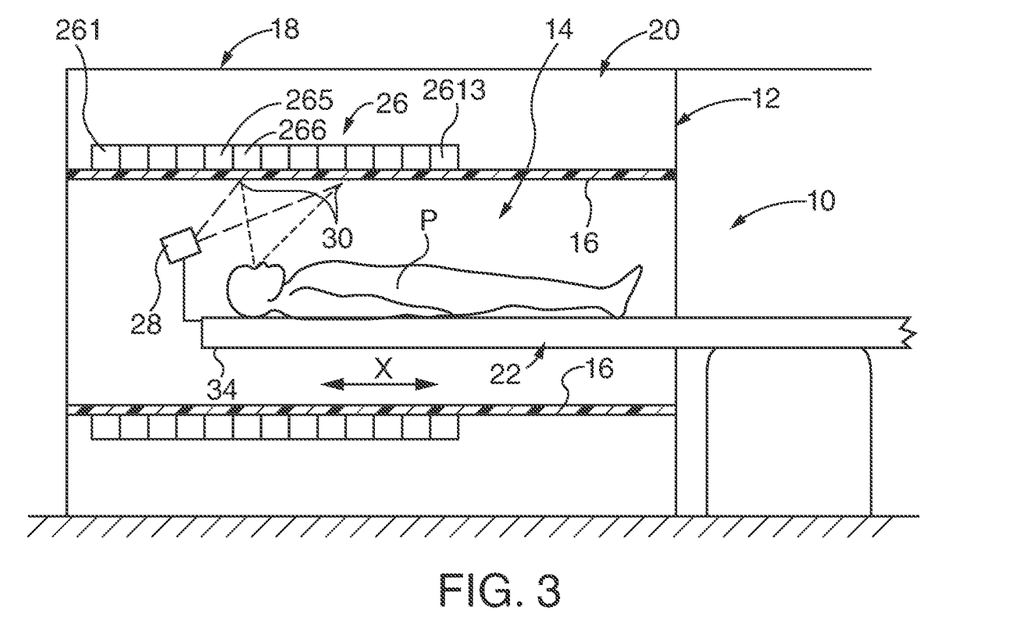
FIG. 3 is an axial cross-sectional view of the medical imaging apparatus of FIG. 1, showing a patient on the patient table in a second axial scanning position in the PET scanning portion of its imaging tube.
Figure 4:
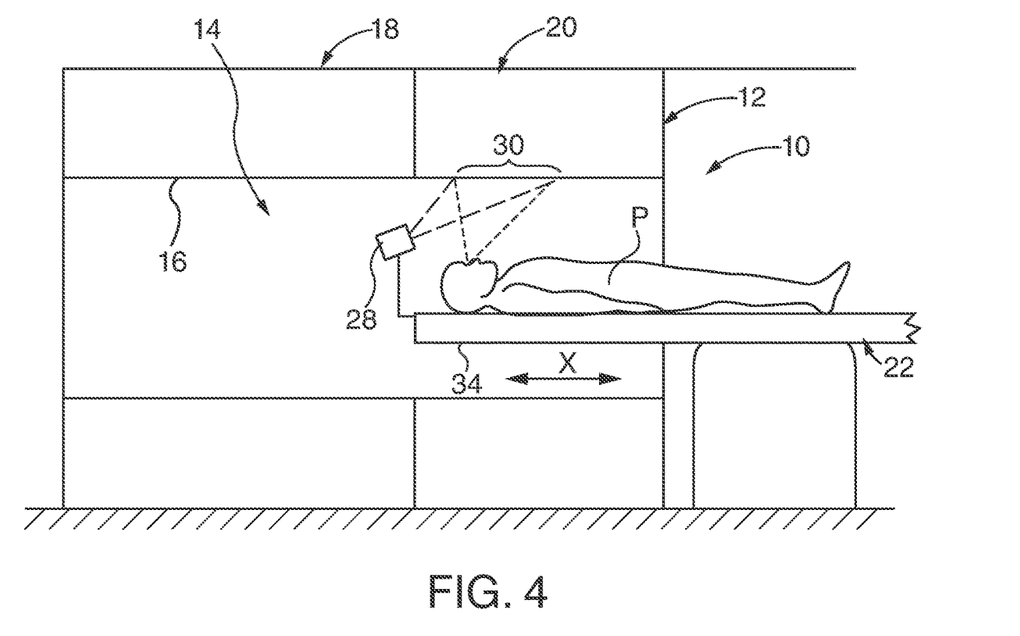
FIG. 4 is an axial cross-sectional view of the medical imaging apparatus of FIG. 1, showing a patient on the patient table in the CT scanning portion of its imaging tube.

FIGS. 2 and 3 show a column of thirteen detector heads located at the twelve o'clock circumferential position in the radiation detector array 26; these include detector heads 261-266 and 2613. The PET scanner portion of the imaging apparatus 10 is constructed and functions in known fashion. A radiation emitting tracer absorbed by the patient emits positrons that are detected by detector heads in the radiation detector array. Detector heads in the detector array 26 that sense patient-emitted positrons are designated to be within an imaging line of response of detectors. For example, when the patient P is on the patient table 22 in the axial position shown in FIG. 2, detector head 262 defines the left-most axial side of the imaging line of response of detectors, while detector head 2613 defines the right-most axial side of the same imaging line of detectors. In FIG. 3, the patient P is now positioned closer to the CT scanning field portion 20 of the imaging apparatus 10. Detector head 266 now defines the left-most axial side of the imaging line of response of detectors, while detector head 2613 defines the right-most axial side of the line. During many PET scanning procedures, the patient table 22 translates left and right along the translation axis X, so various detector heads within a column of detectors are part of the outside of the imaging line of response of detectors.

Figure 1:
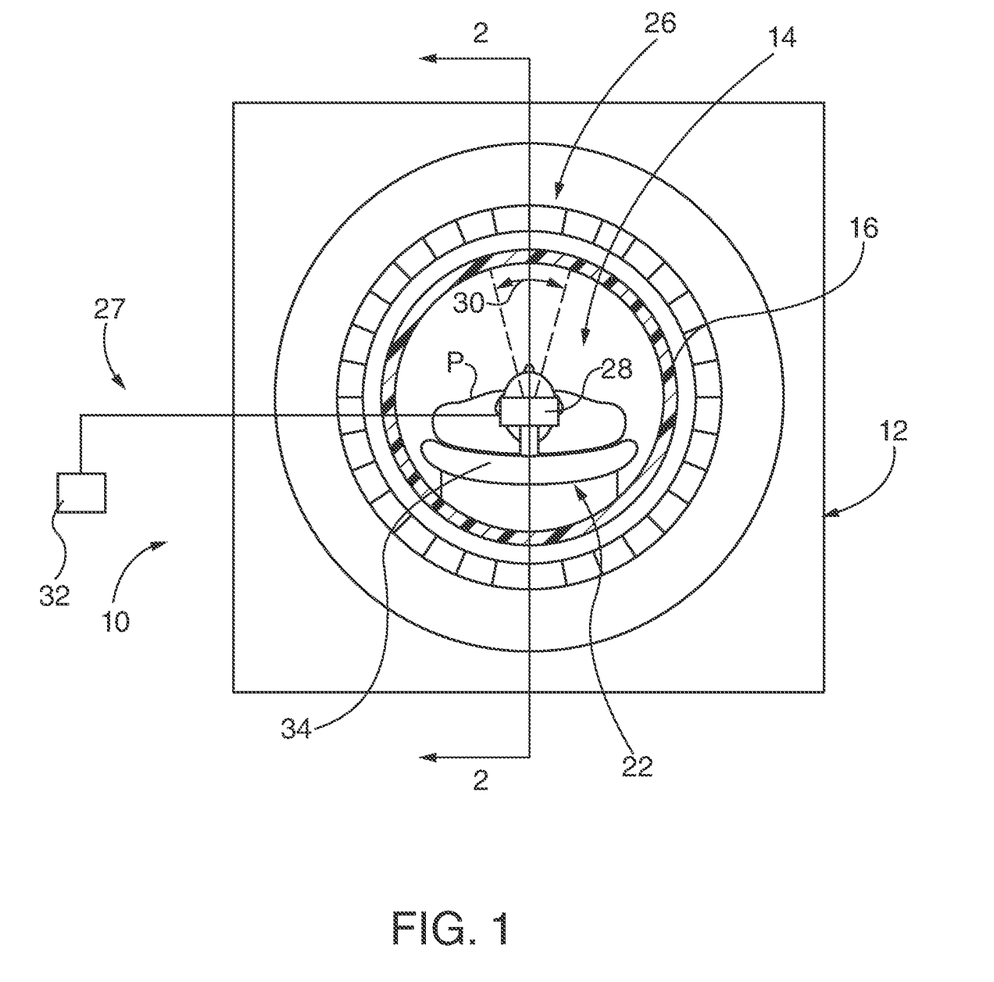
FIG. 1 is an end elevational view of a dual PET/CT modality, medical imaging apparatus that incorporates an embodiment of a patient display system, with the visual imaging projector coupled to the head end of its patient table, projecting the visual image into its imaging tube.

In FIG. 1, the patient imaging system 27 includes a projector 28 for projecting a visual image 30 that is visible to a patient P lying on the patient table 22, during a diagnostic imaging procedure. In all the figures, boundaries of the projected image 30 are shown in long dashed lines, while the portion of the patient's field of view that is relevant for viewing the projected image is shown in shorter dashed lines. The projector 28 is an off-the shelf, portable video projector that is typically used for projecting viewable images on walls, ceilings, viewing screens and other surfaces. In some embodiments, the projector 28 flattens projected images so that they appear flat when projected on a curved surface, such as that of the imaging tunnel wall 16.

The projector 28 projects images obtained from a non-transient image file stored in personal computer 32. In other embodiments, the projector 28 obtains a non-volatile image file stored in another type of accessible image storage device, such as a smart phone, tablet computer, SD card, flash drive, or portal in communication with wired or wireless communications networks. In some embodiments, the communications networks include local area networks and the Internet. In some embodiments, the stored image is stored in a memory device within the projector. In some embodiments, the projected image includes one or more of patient instructions, mood-enhancing images or lighting, or entertainment videos. In FIGS. 2-8, only the projector 28 of the patient imaging system is shown, but it is coupled to an internal or an external image storage device that stores the visual image.

In FIGS. 1-4, the projector 28 is coupled directly to the head end 34 of the patient table 22, by a mounting fixture 36. The mounting fixture 36 includes tilt 38 and pan 40 adjustment mechanisms for orienting the projected visual image 30 in a desired location along the patient tunnel wall 16 (also referred to as an imaging tunnel wall or a scanning tunnel wall), within the patient or imaging tunnel passage 14 of the extended FOV, PET/CT imaging apparatus 10. The mounting fixture 36 orients the projector 28 on the patient table 22 an axial distance away from the patient P, so that it remains outside of imaging line of response of the relevant detectors that are acquiring patient image data during an imaging scan. In this way, the projector 28 does not potentially distort or otherwise degrade image data acquired by detectors in the imaging line of response. For example, in FIG. 2 the projector is located to the left of the detector head 262 that is the first detector in the row of detectors acquiring a PET image of the patient P. When the patient table is in the position shown in FIG. 2, detector head 261 is not presently in the imaging line of response for this PET scan. In contrast, when the patient table 22 is in the position shown in FIG. 3, detector heads 261-265 are not presently in the imaging line of response for the PET scan, so orientation of the projector 28 under any of them does not distort the acquired scan data. In many types of scanning protocols, the patient table translates back and forth along the axis X, shifting the imaging line of response, during a scanning procedure. Similarly, in FIG. 4, the patient is undergoing a CT scanning procedure, where the projector 28 remains outside the imaging line of response of the CT scanning field 20. By mounting the projector 28 at a fixed position on the head end 34 of the patient table 22, its projected image 30 FOV (long dashed lines in all figures) remains at a constant position relative to the patient's own visual FOV (short dashed lines in all figures), as both the projector and the patient P are positioned on the same, moving patient table.

Figure 5:
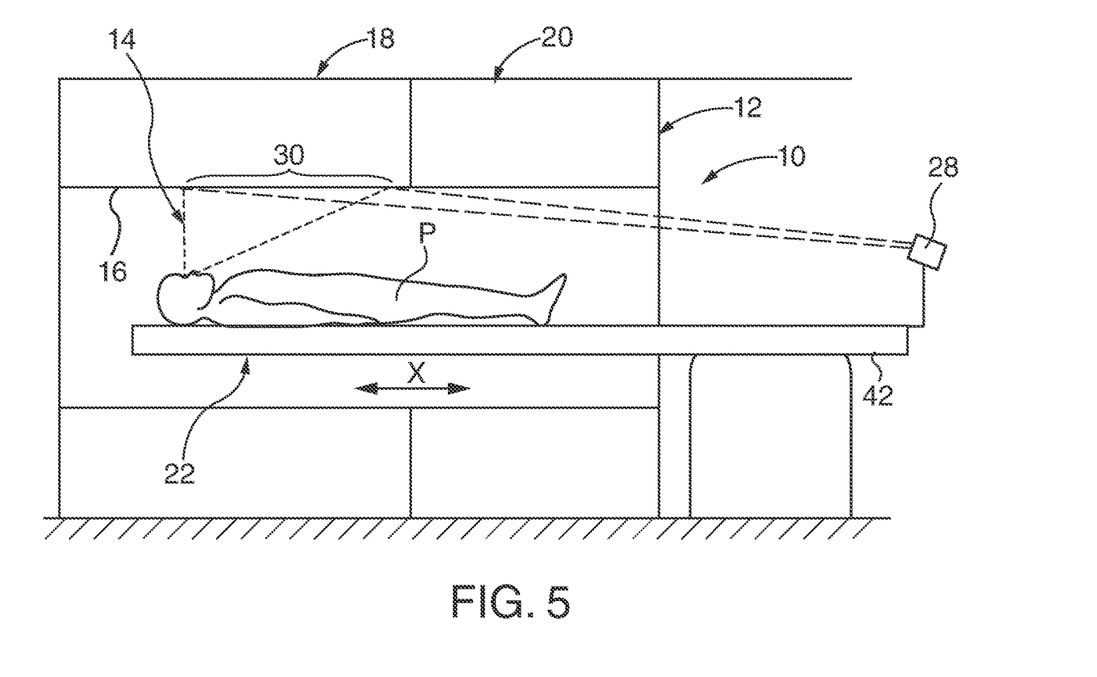
FIG. 5 is an axial cross-sectional view of a dual PET/CT modality, medical imaging apparatus that incorporates another embodiment of a patient display system, with the visual imaging projector coupled to the foot end of its patient table, projecting the visual image into its imaging tube.
Figure 6:
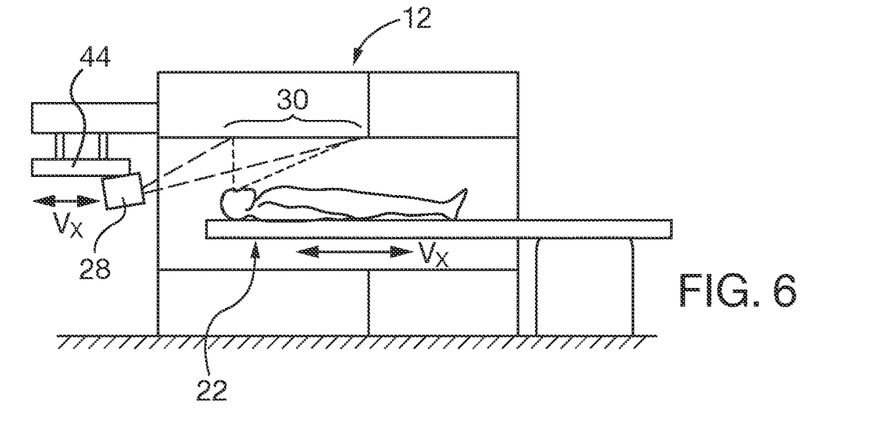
FIG. 6 is an axial cross-sectional view of a dual PET/CT modality, medical imaging apparatus that incorporates another embodiment of a patient display system, with the visual imaging projector coupled to a translatable rail whose translation velocity is in tandem with the translation velocity of the its patient table, the projector projecting the visual image into its imaging tube.
Figure 7:
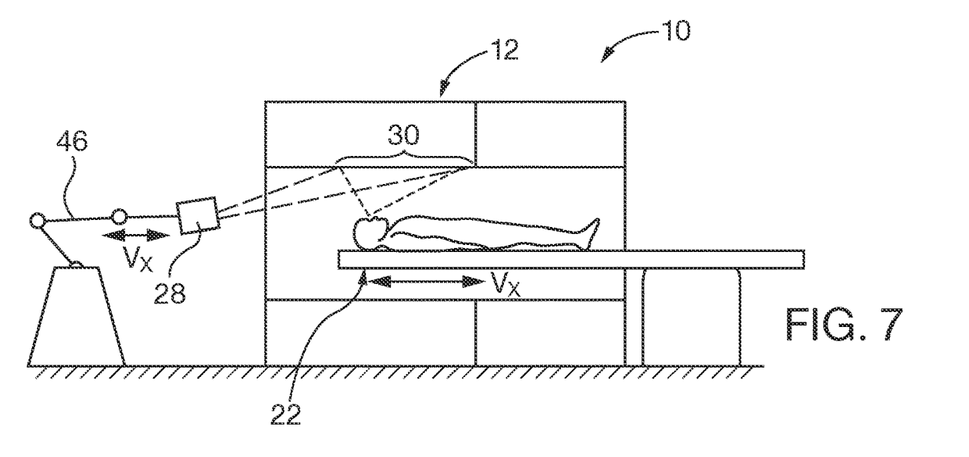
FIG. 7 is an axial cross-sectional view of a dual PET/CT modality, medical imaging apparatus that incorporates another embodiment of a patient display system, with the visual imaging projector coupled to a robotic, multi-link arm whose translation velocity is in tandem with the translation velocity of its patient table, the projector projecting the visual image into its imaging tube.
Figure 8:
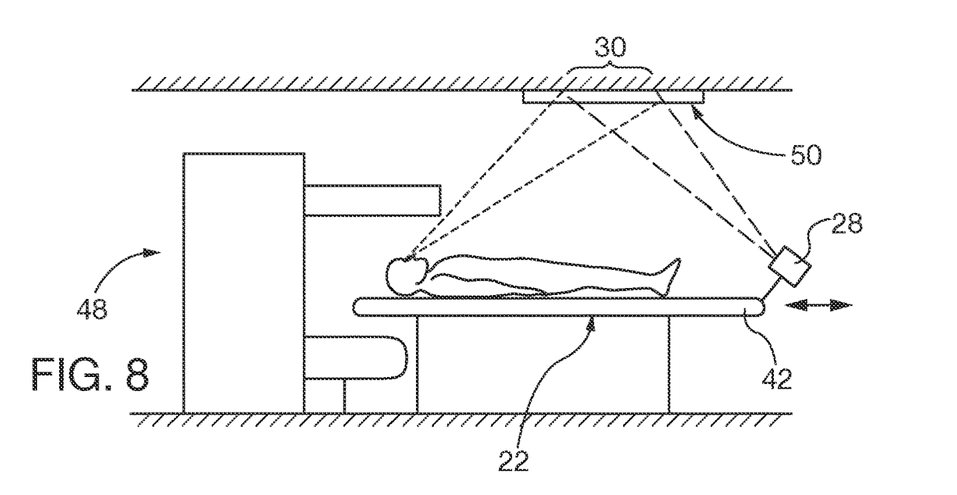
FIG. 8 is side elevational view of a dual SPECT/CT modality, medical imaging apparatus that incorporates another embodiment of a patient display system, with the visual imaging projector coupled to the foot end of its patient table, with the visual image projected on a ceiling screen above the patient table.

In other embodiments the projector 28 is coupled to the imaging system 10 at locations other than at the head end 34 of the patient table 22. In FIG. 5, the projector 28 is coupled to the foot 42 of the patient table at a fixed position and remains outside the respective imaging lines of response of the PET 18 and the CT 20 scanning fields. As with the head end 34 of patient table 22, projector mounted embodiments of FIGS. 1-4, the projector image 30 and the patient FOV remain in the same relative constant position as the table translates during scanning procedures. In other embodiments, the projector is not mounted directly to the patient table 22. In the embodiment of FIG. 6, the projector 28 is coupled to a translatable linear motion track 44, where the track is shown directly coupled to the gantry 12. The linear motion track 44 is in communication with the motion control system of the patient table 22 (not shown) and translates the projector 28 in tandem with the patient table, at the same acceleration and velocity speed/direction $V_X$. In FIG. 7, the projector is coupled to a robotic arm 46 and the robotic arm is indirectly coupled to the scanning apparatus 10 and the gantry 12 by their common affixation to the floor of the imaging room. The robotic arm 46 is in communication with the motion control system of the patient table 22 (not shown) and translates the projector 28 in tandem with the patient table, at the same acceleration and velocity speed/direction $V_X$.

In exemplary embodiments of the patient display system, the projected image is in a location visible to the patient. In the embodiments of FIGS. 1-7, the visible image 30 is projected on the imaging tunnel wall 16 within the patient or imaging tunnel passage 14 of the extended FOV, PET/CT imaging apparatus. In the tunnel-less medical imaging SPECT/CT apparatus 48 of FIG. 8, the projector 28 is mounted at the foot 42 of the patient table 22, and projects the visible image 30 on a ceiling-mounted screen 50, above the patient table, moving in tandem with the patient table. In the embodiments of FIGS. 1-8, the projector 28 directly projects the visual images in the boundaries of the projected image 30. As used in this disclosure, "direct" projection is defined as projection of an image beam from the projector 28, on the imaging tunnel wall 16 of FIGS. 1-7, or on any other patient visible surface, such as the overhead screen 50 of FIG. 8, or a wall or ceiling of the imaging room, without any optical devices, such as lenses, mirrors, or prisms, intermediate the projector and the viewing wall/surface that intentionally distort or redirect the projected visual image 30. In other embodiments, not shown, optical devices, such as lenses, mirrors, or prisms, are located intermediate the projector and the viewing wall/surface that intentionally distort or redirect the projected visual image 30. Transparent or semi-opaque hygienic screens, draperies, or the like, interposed between the projector 28 and the viewing wall 16/surface 50 do not intentionally distort the projected visual image 30.

While FIGS. 1-8 have described operation of the patient display systems in dual-modality PET/CT apparatus 10 or the SPECT/CT imaging apparatus 48, other embodiments of the display system are incorporated and used within other medical imaging modalities, such as CT, DR, MRI, PET, SPECT, PET/MRI, and SPECT/MRI imaging apparatus. In MRI apparatus, embodiments of the projector and related mounting hardware are approved for use in the high-intensity magnetic flux environment of the MRI imaging room. In some embodiments, the patient display system is used with a stationary or static patient table, in which case the projector is also stationary, but located outside the medical scanner's imaging line of response of detectors that are in use during an imaging scanning procedure. While incorporation of the projector 28 in the embodiments of FIGS. 1-8 have been shown with medical imaging apparatus, they are also applicable to radiotherapy apparatus or combination imaging/radiotherapy apparatus (e.g., in image-guided radiotherapy apparatus), by a projector projecting a visible image in a patient tube or on a screen.

In all embodiments of imaging and/or radiotherapy apparatus having moving patient tables, the projected visible image 30 moves in tandem with the patient P on the patient table 22, so that it appears relatively motionless to the patient. In some embodiments, the projector 28 is directly coupled to the patient table 22, while in other embodiments, the projector is directly or indirectly coupled to the medical apparatus and/or its gantry (e.g., the scanner 10 and gantry 12), but it moves in tandem with the acceleration and velocity of the patient table 22.

When the patient display is in use in a medical imaging and/or radiotherapy apparatus, visual images are projected into the patient tunnel or imaging tunnel or scanning tunnel of the apparatus, or on a screen above the patient. Visual images include, by way of non-limiting example, patient instructions (e.g., "please hold your breath" or "please stay motionless"), patient information (e.g., "five minutes left to complete this procedure"), stationary or transient mood lighting, informational or entertainment videos, or the like. Projected, written patient information and/or instruction images are helpful for assuring that the patient comprehends what needs to be done during the imaging or radiotherapy procedure, when background noise and sound attenuation features of the medical apparatus hamper her or his hearing of oral instructions. This is especially helpful for hearing impaired patients. Non-instructional, projected visual images, including by way of non-limiting example mood lighting or soothing pictorial images and entertainment videos, are helpful for distracting a patient before and/or during the imaging or radiotherapy procedure, to avoid or reduce emotional discomfort associated with undergoing the procedure, or coping with restrained movement and/or confinement. An emotionally calmer patient is less likely to make unintentional or intentional body movements during a procedure, which is beneficial for image scan quality and/or targeting of radiotherapy beams.

Although various embodiments that incorporate the invention have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted", "connected", "supported", and "coupled" and variations thereof are to be interpreted broadly; they encompass direct and indirect mountings, connections, supports, and couplings. Further, "connected" and "coupled" are not restricted to physical, mechanical, or electrical connections or couplings.

What is claimed is:

1. A patient display system for a medical imaging apparatus, comprising:
   a gantry, including therein an electromagnetic radiation source and at least one radiation detector, which together generate a diagnostic imaging field including an imaging line of detector response therebetween;
   a patient table selectively translatable through the diagnostic imaging field of the gantry at a first velocity;
   a translatable visual image projector, accessing a visual image, for projecting the visual image on a surface above the patient table in a location that is visible to a patient lying on a patient table, without any optical devices intermediate the projector and the surface that intentionally distort or redirect the projected visual image;
   the projector translating in tandem with the patient table, so that the projected visual image translates in tandem at the first velocity, and appears motionless relative to the patient table; and
   the entire projector always remaining outside the imaging line of detector response in the imaging field where the apparatus is acquiring patient image data.

2. The system of claim 1, the gantry further comprising:
   a patient tunnel through which the diagnostic imaging field is generated;
   a plurality of rows and columns of radiation detectors circumscribing the patient tunnel, each respective detector emitting electrons in response to incident electromagnetic radiation from the radiation source and establishing a respective imaging line of detector response; and
   the projector projecting the visual image directly on a wall surface of the patient tunnel.

3. The imaging system of claim 2, further comprising the projector directly coupled to the patient table.

4. The imaging system of claim 2, further comprising the projector coupled to a translatable track or robot arm located outside the gantry, translating at a second velocity in tandem with the patient table, so that the projected visual image translates in tandem at the first velocity, and appears motionless relative to the patient table.

5. The imaging system of claim 2, further comprising a projector mount coupled to the projector, the projector mount selectively adjusting tilt and/or pan orientation of the projected visual image.

6. The imaging system of claim 1, further comprising the projector directly coupled to the patient table.

7. The imaging system of claim 1, further comprising the projector coupled to a translatable track or robot arm located outside the gantry, translating at a second velocity in tandem with the patient table, so that the projected visual image translates in tandem at the first velocity, and appears motionless relative to the patient table.

8. The imaging system of claim 1, further comprising a projector mount coupled to the projector, the projector mount selectively adjusting tilt and/or pan orientation of the projected image.

9. The imaging system of claim 2, further comprising:
   the gantry generating a plurality of imaging lines of detector response collectively generating a diagnostic imaging field having an extended field of view, through the patient tunnel, the tunnel having an axial length greater than one meter.

10. The imaging system of claim 9, further comprising the projector directly coupled to the patient table.

11. The imaging system of claim 9 in a dual-mode medical imaging apparatus, further comprising the gantry generating sequentially, through the imaging tunnel, separate axially adjacent, respective pluralities of first and second imaging lines of detector responses of respective first and second imaging fields; the entire projector always remaining outside the respective imaging lines of detector response of any imaging field where it is acquiring patient image data.

12. The imaging system of claim 11, further comprising the projector directly coupled to the patient table.

13. The imaging system of claim 11, further comprising the projector coupled to a translatable track or robot arm located outside the gantry, translating at a second velocity in tandem with the patient table, so that the projected visual image translates in tandem at the first velocity, and appears motionless relative to the patient table.

14. A method for displaying a visual image to a patient during a diagnostic imaging scanning procedure with a medical imaging apparatus, comprising:
generating a diagnostic imaging field, with an electromagnetic radiation source and at least one radiation detector, which together generate an imaging line of detector response therebetween, in a gantry of a medical imaging apparatus;
selectively translating at a first velocity, a patient on a patient table through the diagnostic imaging field generated within the gantry, so that the apparatus acquires patient image data in the imaging line of response;
projecting a visual image on a surface above the patient table in a location that is visible to a patient lying on a patient table, with a translatable visual image projector that is located outside the imaging line of detector response when the apparatus is acquiring image, without any optical devices intermediate the projector and the surface that intentionally distort or redirect the projected visual image; and
translating the projector in tandem with the patient table, so that the projected visual image translates in tandem at the first velocity and appears motionless relative to the patient table; and
the entire projector always remaining outside the imaging line of detector response in the imaging field where the apparatus is acquiring patient image data.

15. The method for displaying a visual image of claim 14, the projected visual image comprising patient instructions, and/or patient information about the scanning procedure, and/or stationary mood lighting, and/or transient mood lighting, and/or informational videos, and/or entertainment videos.

16. The method for displaying a visual image of claim 14, the gantry further comprising:
a patient tunnel through which the diagnostic imaging field is generated;
a plurality of rows and columns of radiation detectors circumscribing the patient tunnel, each respective detector emitting electrons in response to incident electromagnetic radiation from the radiation source and establishing a respective imaging line of detector response;
and the projector projecting the visual image directly on a wall surface of the patient tunnel.

17. The method for displaying a visual image of claim 16 in a dual-mode medical imaging apparatus, further comprising:
generating sequentially, through the patient tunnel of the gantry, separate axially adjacent, respective pluralities of first and second imaging lines of detector responses of respective first and second diagnostic imaging fields, the patient tunnel having an axial length greater than one meter; and
the entire projector always remaining outside the imaging line of detector response of any imaging field where it is acquiring patient image data.

18. The method for displaying a visual image of claim 17, the visual image comprising patient instructions, and/or patient information about the scanning procedure, and/or stationary mood lighting, and/or transient mood lighting, and/or informational videos, and/or entertainment videos.

19. A patient display system for a dual modality, PET/CT medical imaging apparatus, comprising:
a gantry including:
an extended field-of-view imaging tunnel, having an axial length greater than one meter,
a PET diagnostic imaging system, having a first electromagnetic radiation source and a plurality of rows and columns of first radiation detectors circumscribing the patient tunnel, which together generate a PET diagnostic imaging field, each respective first detector emitting electrons in response to incident electromagnetic radiation from the first radiation source and establishing a respective first imaging line of detector response therebetween; and
a CT diagnostic imaging system, axially adjacent the PET system, the CT system having a second electromagnetic radiation source and a plurality of rows and columns of second radiation detectors circumscribing the patient tunnel, which together generate a CT diagnostic imaging field, each respective second detector emitting electrons in response to incident electromagnetic radiation from the second radiation source and establishing a respective second imaging line of detector response therebetween;
a patient table selectively translatable, at a first velocity, through the imaging tunnel, in either of the PET or CT diagnostic imaging fields;
a translatable visual image projector, accessing a visual image, for projecting the visual image on a wall of the imaging tunnel in a location that is visible to a patient lying on the patient table, without any optical devices intermediate the projector and the wall that intentionally distort or redirect the projected visual image;
the projector translating in tandem with the patient table, so that the projected image translates in tandem at the first velocity, and appears motionless relative to the patient table; and
the entire projector always remaining outside the respective imaging line of detector response of one of the respective imaging fields where the apparatus is acquiring patient image data.

20. A patient display system for a medical imaging and a radiotherapy apparatus, comprising:
a gantry having an imaging system including therein an electromagnetic radiation source and at least one radiation detector, which together generate a diagnostic imaging field including an imaging line of detector response therebetween and a radiation therapy system generating a therapy beam-zone;
a patient table in the diagnostic imaging field or the therapy beam zone of the gantry;
a visual image projector, accessing a visual image, for projecting the visual image directly above the patient table in a location that is visible to a patient lying on a patient table, without any optical devices intermediate the projector and the wall that intentionally distort or redirect the projected visual image;
the entire projector always remaining outside the imaging line of detector response in the imaging field where the apparatus is acquiring patient image data or outside the radiation therapy beam zone during beam generation.

21. The system of claim 20, the gantry further comprising a patient tunnel through which the imaging line of detector response and/or the radiation therapy beam is generated; and the projector projecting the visual image directly on a wall surface of the patient tunnel.

22. A patient display system for a medical imaging and a radiotherapy apparatus, comprising:
a gantry, having an imaging system including therein an electromagnetic radiation source and at least one radiation detector, which together generate a diagnostic imaging field including an imaging line of detector response therebetween and a radiation therapy system generating a therapy beam-zone;

a patient table selectively translatable through the diagnostic imaging field and the therapy beam zone of the gantry at a first velocity;

a translatable visual image projector, accessing a visual image, for projecting the visual image on a surface above the patient table in a location that is visible to a patient lying on a patient table, without any optical devices intermediate the projector and the wall that intentionally distort or redirect the projected visual image;

the projector translating in tandem with the patient table, so that the projected visual image translates in tandem at the first velocity, and appears motionless relative to the patient table; and the entire projector always remaining outside the imaging line of detector response in the imaging field where the apparatus is acquiring patient image data or outside the therapy beam zone of the gantry during beam generation.

23. The system of claim 22, the gantry further comprising a patient tunnel having an axial length greater than one meter, through which the imaging line of detector response and/or the radiation therapy beam is generated; and the projector projecting the visual image directly on a wall surface of the patient tunnel.

* * * * *